United States Patent [19]

Tracy et al.

[11] Patent Number: 4,640,627

[45] Date of Patent: Feb. 3, 1987

[54] APPARATUS FOR MONITORING A PLASMA TORCH

[75] Inventors: David H. Tracy, Norwalk; Michael J. O'Brien, Bethel; Walter Bohler, Wilton, all of Conn.

[73] Assignee: The Perkin-Elmer Corporation, Norwalk, Conn.

[21] Appl. No.: 526,758

[22] Filed: Aug. 26, 1983

[51] Int. Cl.⁴ .............................................. G01J 5/10
[52] U.S. Cl. ................... 374/121; 250/342; 250/354.1; 219/121 PT; 375/30
[58] Field of Search ............ 250/338, 349, 342, 354.1; 374/121, 127, 130, 128, 126; 340/600; 356/43, 316; 219/121 PT

[56] References Cited

U.S. PATENT DOCUMENTS 3,766,781  10/1973  Roberts ............................. 374/128
3,817,622   6/1974  Billman et al. ...................... 356/43
3,891,847   6/1975  Schmidt et al. .................... 250/338
4,256,404   3/1981  Walker ............................... 356/316
4,283,934   8/1981  Siess .................................. 374/126

OTHER PUBLICATIONS

Hunn, "A Transpiration Radiometer for Measurement of Total Thermal Radiation from a Flowing Plasma", Proc. 18th International ISA Aerospace Instru. Sym., vol. 18, Miami, Florida, May 15-17, 1972, pp. 131-135.

Primary Examiner—Carolyn E. Fields
Attorney, Agent, or Firm—E. T. Grimes; T. P. Murphy; F. L. Masselle

[57] ABSTRACT

An apparatus for monitoring a plasma torch includes a dedicated photometer which produces a signal representative of the temperature of a quartz tube of the torch, which signal can be used to reduce the temperature thereof.

10 Claims, 3 Drawing Figures

APPARATUS FOR MONITORING A PLASMA TORCH

BACKGROUND OF THE INVENTION

The present invention generally relates to an apparatus for monitoring a plasma torch and, in particular, relates to such an apparatus which includes a means for reducing the temperature thereof.

One of the more significant recent advances in the field of atomic spectroscopy is generally referred to as plasma emission spectroscopy. In such a system, the sample is heated by means of a plasma discharge to such a high temperature that atomic emission occurs. During atomic emission some of the electrons of an atom are, by the thermal energy imparted thereto, raised to a higher energy level. Upon decay, i.e., an electron returning to a lower energy level, a photon of light is emitted. This emitted light propagates at a specific wavelength which is characteristic of the particular element. Consequently, by determining the intensity of the light emitted at a characteristic wavelength, the concentration of particular element can be determined. Such an analytical technique is probably most advantageous for refractory elements that are relatively insensitive to other atomization techniques. This advantage derives from the high temperatures inherently associated with a plasma torch, i.e., on the order of about 5000° C.

The most conventional form of plasma torch presently in use is generally referred to as an inductively coupled plasma (hereinafter ICP). The gases necessary to sustain an ICP are commonly introduced into a torch constructed of quartz. The high temperature plasma discharge is partially contained by a quartz tube. In such a torch, a quartz tube surrounds the torch to shape the plasma, which torch is ignited and maintained by means of a strong radio frequency (RF) field. The RF field is created by an RF load coil through which the gases are fed.

Because of the ability of ICP discharges to reach very high temperatures which can easily exceed the melting temperature of quartz, the torch should be carefully monitored to prevent damage thereto. Excessive heating of the outer quartz tube generally occurs either during start-up or when insufficient gas flow is provided.

It is difficult to measure the tube wall temperature for at least three reasons. First, it is difficult to provide any direct contact monitor to the quartz because of the high temperature thereof. Second, any form of electronic monitoring within the torch chamber is difficult due to the strong electromagnetic fields near the RF coil. Third, during the start-up of the torch, which occurs within the quartz tube, excessive temperatures can be reached quickly and without detection by conventional techniques. Additionally, since the ability to remove and/or replace the torch is a desirable convenience it is important not to complicate that procedure by including unnecessary devices within the torch chamber.

SUMMARY OF THE INVENTION

Accordingly, it is one object of the present invention to provide an assembly for monitoring a plasma torch which avoids the above-recited difficulties.

This object is achieved, at least in part, by an apparatus including a remotely located electro-optical detector and a means for extinguishing the plasma.

Other objects and advantages of the present invention will become apparent from the following detailed description read in conjunction with the appended claims and the drawing attached hereto.

BRIEF DESCRIPTION OF THE DRAWING

The drawing, not drawn to scale, includes.

DETAILED DESCRIPTION OF THE INVENTION

Figure 1:
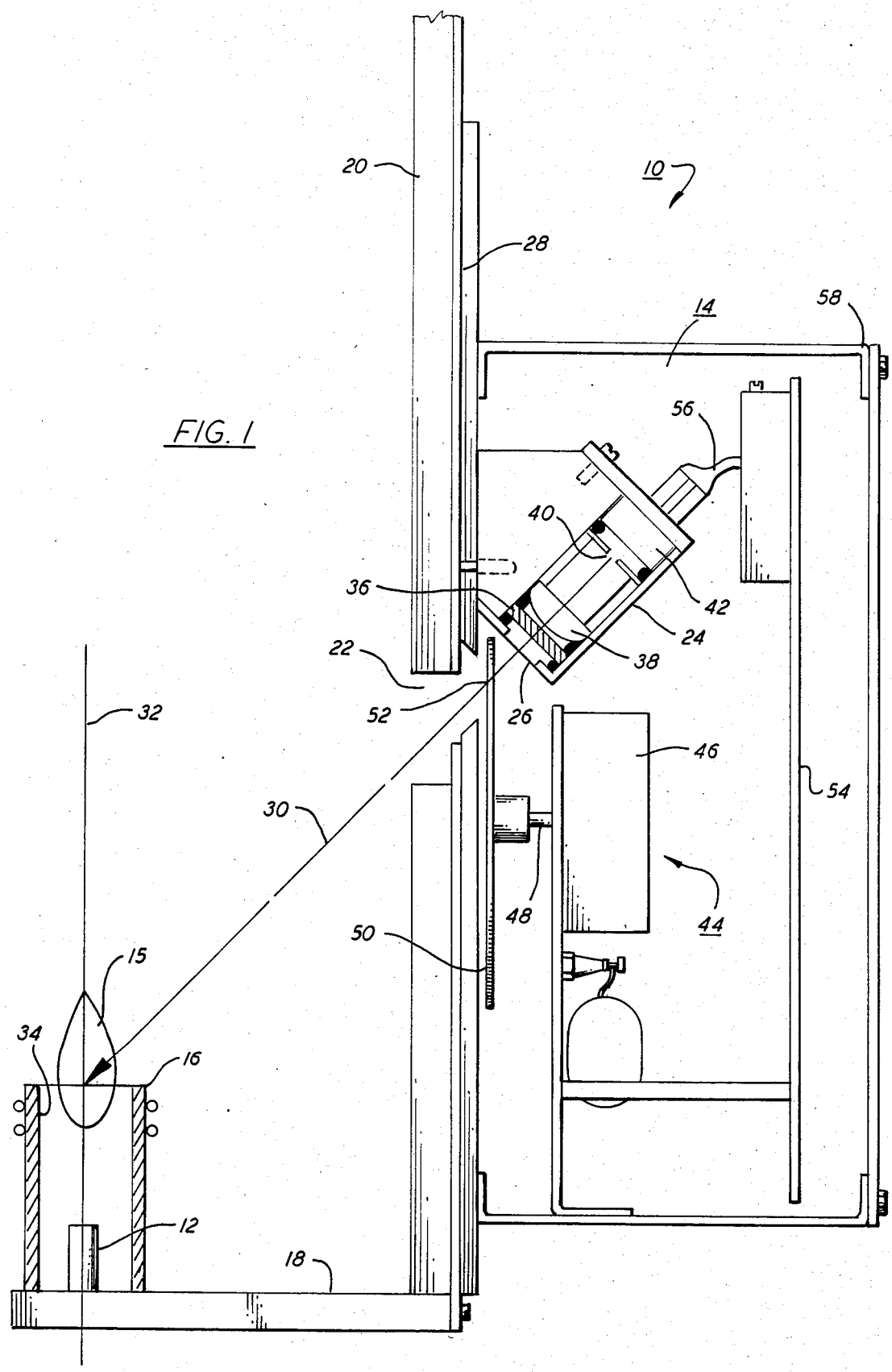
FIG. 1—which is a pictorial lay-out of an apparatus embodying the principles of the present invention.

An assembly, generally indicated at 10 in FIG. 1, includes a plasma torch 12 having an outer quartz tube 16 and an apparatus 14 for monitoring the temperature of the tube 16 of the torch 12, which apparatus 14 embodies the principles of the present invention.

As shown in FIG. 1, a plasma discharge 15 is concentrically surrounded by the quartz tube 16 and positioned within a torch chamber 18. One wall 20 of the torch chamber 18 being provided with an opening 22 therethrough.

A detector body 24 having an entrance aperture 26 is affixed to the external surface 28 of the wall 20. The body 24 is mounted such that infrared (IR) radiation emitted from the exterior surface of the quartz tube 16 passes through the opening 22 and through the aperture 26 thereof. Preferably, the body 24 is mounted such that the longitudinal axis 30 thereof is at an angle of about 45° with respect to the axis 32 of the plasma torch 12. In practice, the angle need not be 45° although by so mounting the body 24, light emitted from the inner surface 34 of the tube 16 is also viewed by the aperture 26. Thus, localized hot spots inside the tube 16 will be detected.

In the preferred embodiment, the detector body 24 includes a filter 36, a lens 38, an aperture stop 40 and a detector 42. The filter 36, lens 38, aperture stop 40 and detector 42 are preferably all coaxial with the axis 30 of the detector body 24 and aligned with the entrance aperture 26.

In one embodiment, the filter 36, is commercially available and selected to pass wavelengths from between about 8 micrometers to about 15 micrometers. The lens 38 is preferably a potassium bromide, i.e., KBr, lens having a focal length of about 13 millimeters. The aperture stop 40 has a diameter of about 0.5 millimeters and is spaced apart from lens 38 by about 11.6 millimeters.

The detector 42 is preferably a lithium tantalate type of pyroelectric detector which produces an electronic signal based upon charge migration. One such detector is the Eltec 408, manufactured and marketed by Eltec Instruments Inc. of Daytona Beach, Fl. In order to detect temperature changes with such a detector 42 the source of radiation being detected must be modulated. Thus, in the preferred embodiment, a chopper mechanism 44 is provided which includes a motor 46 for rotating a shaft 48 to which is affixed a chopper blade 50 having regularly spaced openings 52 therein. The mechanism 44 is located so that the openings 52 pass through the axis 30 of the detector body 24 whereby any radiation entering the body 24 via the entrance aperture 26 is modulated. Consequently, the detector 42 produces a square wave electronic signal. In the preferred embodiment, the rotational velocity of the chopper blade 50 and the number of openings 52 therein are so coordinated that the square wave from the detector 42 has a frequency of about 10 Hz. This signal is provided to a circuit board 54 via an electrical conduit 56.

As shown, the detector body 24, the chopper mechanism 44 and the circuit board 54 are all mounted and contained within an enclosure 58 affixed to the wall 20 of the torch chamber 18.

Figure 2:
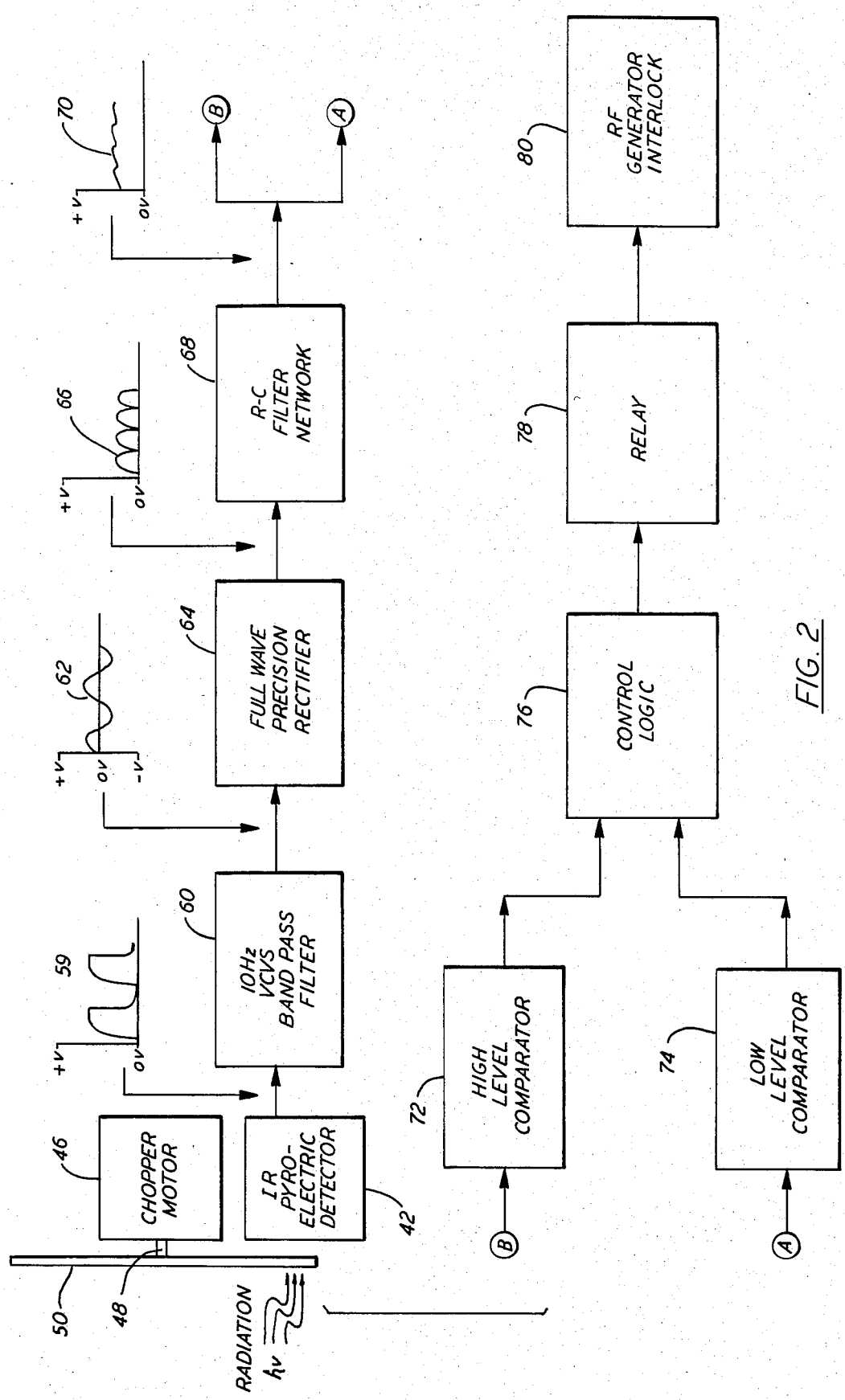
FIG. 2—is a block diagram of the circuit of the apparatus shown in FIG. 1.

Referring to the block diagram of FIG. 2, the square wave, designated at 59, from the detector 42 is filtered by means of an electronic 10 Hz VCVS band pass filter 60 whereby a sine wave 62 is produced. The sine wave 62 is then rectified by a full wave precision rectifier 64 to produce the rectified waveform 66 which is then filtered. That is, the rectified waveform 66 is passed through an R-C filter network 68 which produces therefrom a low ripple d.c. signal 70. The voltage level of the output of the R-C filter network 68 is thus dependent upon the intensity of the radiation reaching the detector 42. As more fully discussed hereinafter the intensity of the radiation reaching the detector 42 is in the infrared spectrum and this is directly related to the temperature of the quartz tube 16.

Figure 3:
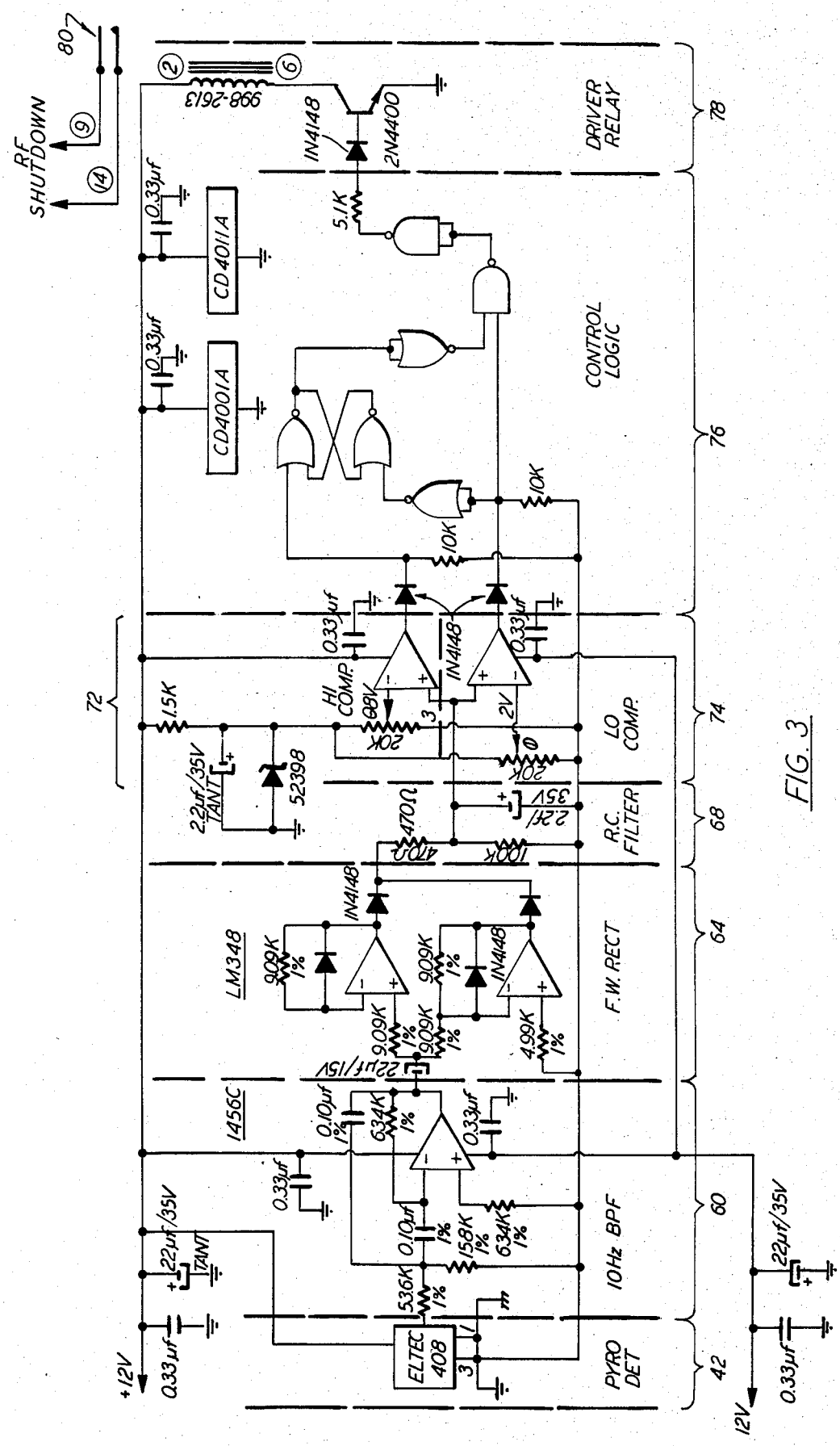
FIG. 3—is a detailed schematic of one embodiment of the block diagram shown in FIG. 2.

The voltage level output from the RC filter network 68 is monitored by a high level comparator 72 and a low level comparator 74. Thus, if the voltage level output from the RC filter network 68 exceeds a preselected voltage, for example about 8.5 volts, the signal from the high level comparator 72 triggers a control logic circuit 76 and a relay 78, and an RF generator interlock 80 to shut off RF source, not shown, and hence the torch 12. When the temperature of the torch 12 falls below a predetermined level, such as 85° C., the voltage level output for the RC filter network 68 drops below a predetermined voltage, for example, 2.5 volts, and a signal from the low level comparator 74 allows use of the torch 12 to be restarted. A more detailed exemplary circuit schematic is shown in FIG. 3. In particular, the low level detector 74 determines the voltage 70 is below the selected lower threshold and produces a signal to control logic 76 indicating that the torch can be reignited. Logic 76 thereafter actuates the relay 78 to close the RF generator interlock 80 thereby causing the RF generator (not shown) coupled thereto to resume operation causing the plasma flame to be ignited again.

The above-described apparatus 14 makes use of the material characteristic of quartz which makes it absorb, i.e., filter, IR radiation, between the wavelengths of about 8.5 micrometers to about 10 micrometers at a safe temperature which temperature depends on the particular batch of quartz used. Consequently, by only detecting radiation in this band of wavelength, by means of filter 36, the temperature of quartz shield is accurately measured without excessive background radiation interference.

The embodiment described herein is exemplary and it is understood that other arrangements and configurations will become apparent to those skilled in the photometry art from a reading hereof. Thus, the present invention is deemed limited and defined only by the appended claims and the reasonable interpretation thereof.

What is claimed is:

1. An apparatus for monitoring the temperature of a quartz tube used to partially surround a plasma flame issuing therefrom comprising; in combination:

electro-optical detector means remote from said quartz tube for producing an electrical signal whose amplitude is a function of the temperature of the quartz tube, said electro-optical detector means being disposed to receive infrared radiation from at least part of the exterior surface of the quartz tube and at least part of the interior surface of the tube; and threshold means responsive to said electrical signal being above an upper threshold level indicative of a temperature approaching the melting point of quartz to produce a signal to turn off the plasma flame issuing from the quartz tube.

2. Apparatus as claimed in claim 1 wherein said detector means includes a filter element selected to pass wavelengths from between about 8 mm to about 15 mm.

3. Apparatus as claimed in claim 1 wherein said detector means includes a photometer having an entrance aperture aligned to receive the infrared radiation from the tube.

4. Apparatus as claimed in claim 3 wherein said photometer further includes:

an aperture stop, said aperture stop being located between said lens and said detector.

5. Apparatus as claimed in claim 4 wherein said detector means includes a filter element selected to pass wavelengths from between about 8 mm to about 15 mm.

6. Apparatus as claimed in claim 3 wherein said detector means includes a filter element selected to pass wavelengths from between about 8 mm to about 15 mm.

7. Apparatus as claimed in claim 1 wherein said threshold means includes means to detect when the temperature of the tube is below a second threshold less than said upper threshold and to eliminate said turn off signal.

8. Apparatus as claimed in claim 7 wherein said detector means includes a filter element selected to pass wavelengths from between about 8 mm to about 15 mm.

9. Apparatus as claimed in claim 1 additionally including a chopper disposed between said detector means and the tube to modulate the infrared radiation impinging on said detector means.

10. Apparatus as claimed in claim 9 wherein said detector means includes a filter element selected to pass wavelengths from between about 8 mm to about 15 mm.

* * * * *